United States Patent [19]
Chan et al.

[11] Patent Number: 6,159,931
[45] Date of Patent: Dec. 12, 2000

[54] LIPID-MODIFIED INSULIN INCORPORATED LIPOSOMES FOR SELECTIVELY DELIVERING CYTOTOXIC AGENTS TO HEPATOMA CELLS

[75] Inventors: Kenneth K. Chan, Dublin; Hong Mei, Columbus, both of Ohio

[73] Assignee: The Ohio State University, Columbus, Ohio

[21] Appl. No.: 09/162,869

[22] Filed: Sep. 29, 1998

[51] Int. Cl.[7] .......................... A61K 38/28; A61K 9/127; C07K 14/62
[52] U.S. Cl. ............... 514/3; 424/450; 530/303; 536/6; 552/201; 552/202
[58] Field of Search .................. 514/3, 963, 23, 514/35; 424/450; 436/829; 530/303; 552/201, 202; 536/6

[56] References Cited

U.S. PATENT DOCUMENTS

| | | | |
|---|---|---|---|
| 4,863,896 | 9/1989 | Geho et al. | 514/4 |
| 5,316,771 | 5/1994 | Barenholz et al. | 424/450 |
| 5,468,400 | 11/1995 | Michlin | 252/21 |
| 5,468,499 | 11/1995 | Chan et al. | 424/450 |
| 5,693,609 | 12/1997 | Baker et al. | 514/3 |

OTHER PUBLICATIONS

Young, Marie, "Incorporation of Insulin into a Liposomal Membrane" Master's Thesis, The Ohio State University, 1982.
Mei, Hong, "Formulation and Cell Uptake of Palmitoyl Insulin Incorporated Liposomal Phosphoramide Mustard" Master's Thesis, The Ohio State University, 1996.
"Stability Characterization and Hypoglycemic Effect of NB1–CIS–9–Hexadecenyl Insulin in Solution" by Mei, et al., Abstract on 1998 American Association of Pharmaceutical Scientists Annual Meeting in San Francisco.
"Lipid Modified Insulin: Site–Specific Synthesis, Separation, Characterization and Biological Activity" by Mei, et al., *Pharmaceutical Research*, 14(11):S156, 1997.
"Synthesis and Purification of NB1–Palmitoyl Insulin" by Tsai, et al., *Journal of Pharmaceutical Sciences*, vol. 86, No. 11, Nov. 1997, pp. 1264–1268.
"Formulation and Cell Uptake of Palmitoyl Insulin Incorporated Liposomal Phosphoramide Mustard" by Hong Mei, Master Thesis, The Ohio State University Graduate School, 1996.
"Incorporation of Insulin Into a Liposomal Membrane" by Regina Marie Young, Master Thesis, The Ohio State University, 1982.
"Palmitoyl Insulin as a Homing Ligand for Targeting Liposomes to Hepatocytes" by Yali J. Tsai, Dissertation, The University of Southern California, Aug. 1992.

*Primary Examiner*—Michael P. Woodward
*Assistant Examiner*—Anish Gupta
*Attorney, Agent, or Firm*—Calfee, Halter & Griswold LLP

[57] ABSTRACT

The present invention provides a lipid-modified insulin comprising an insulin molecule linked to an alkyl group by an amine linkage. Preferably, the alkyl group is a straight chain carbon comprising from about 14 to 20 carbon atoms. Preferably, the alkyl group is linked to the B1 phenylalanine or the B29 lysine. The present invention also provides a liposome comprising such lipid-modified insulin. Preferably, the liposomes are small unilamellar vesicles (SUVs) which have a particle size of less than 100 nm.

The present invention also provides a method for making a lipid-modified insulin. The method comprises reacting the protein with a hydrophobic aldehyde in the presence a reducing agent to provide a lipid-modified insulin in which an amino acid of the insulin is linked to an alkyl group by an amine linkage.

The present invention also relates to a method of killing hepatoma cells, particularly the hepatoma cells that are found in a hepatocellular carcinoma. The method comprises the steps of: providing liposomes containing a cytotoxic agent and having a lipid-modified insulin associated with the lipid bilayer thereof and exposing the hepatoma cells to the liposomes.

21 Claims, No Drawings

LIPID-MODIFIED INSULIN INCORPORATED LIPOSOMES FOR SELECTIVELY DELIVERING CYTOTOXIC AGENTS TO HEPATOMA CELLS

BACKGROUND OF THE INVENTION

Hepatocellular carcinoma is a human cancer with a poor prognosis. Indeed, most patients diagnosed with hepatocellular carcinoma do not live for even a year following diagnosis.

Cytotoxic agents such as phosphoramide mustard (PM) are highly toxic to the malignant cells of the liver, i.e. the hepatoma cells. However, due to its high polarity and chemical instability, PM possesses a short circulation half life and rapid urinary excretion in vivo. Consequently, PM itself is not clinically useful as an anticancer agent for hepatocellular carcinoma. Attempts have been made to overcome the polarity problems of PM by encapsulating this cytotoxic agent into liposomes. However, such liposomes tend to accumulate in the reticuloendothelial system in liver and spleen, thereby limiting their usefulness as vehicles for delivering cytotoxic agents to hepatoma cells.

Hepatoma cells are known to express high levels of insulin receptor as compared to normal hepatocytes and other normal cells. Thus, the insulin receptor is an attractive target for delivering cytotoxic agents to hepatoma cells. Previously, it has been demonstrated that liposomes that have NB1-palmitoyl insulin incorporated therein are selectively taken up by hepatocytes in rodents. Unfortunately, the procedure used for making such liposomes is tedious and time-consuming. Moreover, the procedures currently used to prepare the lipid-modified insulin requires lengthy protection and purification steps. This method, which involves selective modification of reactive sites on the insulin molecule, usually is achieved by blocking other undesired sites. Thus, when synthesizing NB1 palmitoyl insulin or NB29 palmitoyl insulin, undesired free amino groups, typically, are first blocked with t-boc or other similar groups, followed by purification of the insulin derivatives with only the desired reactive amino group open. The purified species is then reacted with palmitic acid hydroxysuccinamide ester. The preparation is completed by deblocking the t-boc groups to free the other unmodified amino groups followed by final purification. Because the synthesis involves a multiple-step reaction, separation, dialysis and lyophylization, the yield of this method is extremely low.

Accordingly, it is desirable to have a modified insulin that can bind to the insulin receptor and that can be incorporated into liposomes for targeting cytotoxic agents to hepatocellular carcinoma cells. A simple method for making the modified insulin is also desirable.

SUMMARY OF THE INVENTION

The present invention provides an improved lipid-modified insulin comprising an insulin molecule linked to an alkyl group by an amine linkage. Preferably, the alkyl group is a straight chain carbon comprising from about 14 to 20 carbon atoms. Preferably, the alkyl group is linked to the B1 phenylalanine or the B29 lysine. The present invention also provides a liposome comprising such lipid-modified insulin. Preferably, the liposomes are small unilamellar vesicles (SUVs) which have a particle size of less than 100 nm.

The present invention also provides a method for making a lipid-modified insulin. The method comprises reacting the protein with an aliphatic aldehyde in the presence a reducing agent to provide a lipid-modified insulin in which an amino acid of the insulin is linked to an alkyl group by an amine linkage.

The present invention also relates to a method of killing hepatoma cells, particularly the hepatoma cells that are found in a hepatocellular carcinoma. The method comprises the steps of: providing liposomes containing a cytotoxic agent and having a lipid-modified insulin associated with the lipid bilayer thereof and exposing the hepatoma cells to the liposomes. The present invention also relates to a method of treating hepatocellular carcinoma. The method comprises the steps of: providing liposomes containing a cytotoxic agent and having a lipid-modified insulin associated with the lipid bilayer thereof, and administering the liposome to a patient with hepatocellular carcinoma.

DETAILED DESCRIPTION OF THE INVENTION

An improved lipid-modified insulin comprising an insulin molecule linked to an alkyl group by an amine linkage is provided. Preferably, the alkyl group comprises from about 14 to 20 straight chain carbon atoms, more preferably from about 16 to 18 straight chain carbon atoms. Preferably, the alkyl group is linked to the B1 phenylalanine or the B29 lysine of the insulin molecule. Such lipid-modified insulin molecules are useful for forming liposomes that are selectively targeted to hepatoma cells, particularly the hepatoma cells that constitute hepatocellular carcinoma. Such lipid-modified insulin molecules are also useful reagents for research purposes, especially in research directed at methods for treating diabetes.

The present invention also provides a liposome comprising a lipid-modified insulin associated with the lipid bilayer thereof. The liposome contains a cytotoxic agent. Suitable cytotoxic agents include but are not limited to phosphoramide mustard, menadione, doxorubicin and daunorubicin. Preferably, the liposomes are small unilamellar vesicles (SUVs) which, more preferably, have a particle size of less than 100 nm. Lipids that are suitable for forming such liposomes include but are not limited to sphingomyelin; cholesterol; the phosphatidylcholines, including, for example, L-α-dimyristoylphosphatidylcholine (DMPC), L-α-dipalmitoylphosphatidylcholine (DPPC) and L-α-distearoylphosphatidylcholine (DSPC); phosphatidylglycerols, including, for example, L-α-dimyristoylphosphatidylglyeerol (DMPG) phosphatidylethanolamines, phosphatidylinositols, and phosphatidic acids containing lauric acid, myristic acid, palmitic acid, palmitoleic acid, stearic acid, oleic acid, linoleic acid, arachidonic acid, behenic acid and lignoceric acid. Preferably, the ratio of cytotoxic drug, particularly PM, to lipid is greater than 0.12 $\mu g/\mu g$. Methods for forming liposomes from such lipids are described in U.S. Pat. No. 5,468,499 issued to Chan et al. on Nov. 21, 1995, which is specifically incorporated herein by reference.

The present invention also relates to a method of killing hepatoma cells, particularly the hepatoma cells that are found in a hepatocellular carcinoma. The method comprises the steps of: providing liposomes containing a cytotoxic agent and having a lipid-modified insulin associated with the lipid bilayer thereof and exposing the hepatoma cells to the liposomes. The lipid-modified insulin of the liposomes comprise an alkyl group which is attached either to the B1 phenylalanine or the B29 lysine of the insulin molecule.

The present invention also provides a method for attaching a straight chain alkyl group to a reactive amino acid of a protein, particularly to a reactive amino acid of insulin. The method comprises adding the protein, particularly insulin, and an aliphatic aldehyde to a aqueous-organic reaction medium, and reacting the protein with the aldehyde in the presence a reducing agent, such as, for example, sodium cyanoborohydride. This reductive alkylation procedure results in the production of a lipid-modified protein comprising a protein linked to an alkyl group by an amine linkage. In a preferred embodiment, the protein is insulin, more preferably human insulin, and the reaction medium comprises sodium salicylate and isopropanol. This one-step procedure is simple, efficient, and does not require the use of protecting agents to make the lipid-modified insulin as is required in the methods of the prior art.

Preferably, the method further comprises a purification step in which the lipid-modified insulin is separated from unmodified insulin by differential C18 solid phase extraction. Such procedure preferably comprises the steps of: applying the reaction mixture to a C18 resin column, eluting the column with a first solution comprising trifluoroacetic acid and methanol, and then with a second solution, preferably comprising trifluoroacetic acid and a greater amount of methanol than the first solution. Preferably, the elution step is accomplished by centrifuging the column after the solutions are applied thereto. This purification procedure is simple, efficient and provides a lipid-modified insulin preparation having a purity of approximately 98%.

A method of producing a lipid-modified insulin which comprises an insulin molecule linked to an alkyl group by an amide linkage is provided. The method comprises acylation of the protein using N-hydroxysuccinimide ester of long chain fatty acid esters without using a reducing agent. The reaction medium in this method preferably comprises sodium salicylate and isopropanol.

A method for entrapping cytotoxic agents, particularly PM and menodione, in liposomes is provided. The method comprises forming multilamellar vesicles (MLVs) using conventional techniques, freezing-drying the MLVs to provide a lipid matrix, hydrating the lipid matrix with a solution containing the cytotoxic drug to provide a liposome preparation, extruding the liposome preparation through at least one membrane having a pore size of about 100 nm or greater and then through at least one membrane having a pore size of less than about 100 nm, preferably from about 50 to 100 nm to provide the liposomes. The ratio of cytotoxic agent to lipid is preferably at least 0.15 $\mu$g of PM to 1.0 $\mu$g of lipid in the liposomes prepared by this method.

The following examples are for purposes of illustration only and are not intended to limit the scope of the claims which are appended hereto.

Preparation of Lipid Modified Insulin

EXAMPLE 1

Five milligrams of insulin (0.87 mmole) was dissolved in a 1.5M sodium salicylate/54% isopropanol, pH 6.8 containing 1.25 mg (5.25 mmole) cis-9 hexadecenal and 110 $\mu$l 50 mM NaBH$_3$CN and the solution was gently shaken at room temperature overnight. The reaction was stopped by dialyzing the reaction mixture against distilled water. The molecular weight cutoff for the dialysis was 3500. The reaction mixture was evaluated by reverse-phase HPLC and Electrospray LCMass Spectrometry (ES LC-MS) to determine the extent of modification, i.e., the percent of the insulin that had one or more alkyl groups linked thereto, and the site of modification, i.e., the amino acid to which the alkyl groups were bound. The results of the HPLC analysis are shown in Table I below.

To separate the lipid-modified insulin from unreacted insulin, the reaction mixture was diluted with 5 ml distilled water and then loaded onto a C 18 column, which was made by packing one gram of Bondesil C18 resin into a 0.8×4 cm Poly-prep column and then centrifuging at 110 g (1000 rpm) for 3 minutes. The eluate was collected and reloaded onto the same column as before. This loading procedure was repeated for eight times. Sodium salicylate was removed by washing the column with distilled water followed by centrifugation. Then the protein components were sequentially eluted by 0.1% TFA with increasing methanol content as described below. Using centrifugation at 200 g (1,300 rpm) for 3 min, the first protein component, referred to hereinafter as "Fraction I", was eluted by 0.1% TFA in 60% methanol; the second protein component, referred to hereinafter as "Fraction II" was eluted by 0.1% TFA in 80% methanol; and the third component, referred to hereinafter as "Fraction III" was eluted by 0.1% TFA 100% methanol. The UV absorbance at 280 nm was used to monitor the elution. The tentative identity and purity of each component was determined by reverse-phase HPLC.

EXAMPLE 2

Five milligrams of insulin was reacted with 1.25 mg (5.25 mmole) cis-9 hexadecenal and 110 $\mu$l 50 mM NaBH$_3$CN as described in Example 1 except that the reaction medium was 0.1 M phosphate sodium buffer, pH 7. The extent of modification and the site of the modification were evaluated by reverse-phase HPLC and Electrospray LCMass Spectrometry (ES LC-MS), as described in Example A. The results of the HPLC analysis are shown in Table I below.

EXAMPLE 3

Five milligrams of insulin was reacted with 1.25 mg (5.25 mmole) cis-9 hexadecenal and 110 $\mu$l 50 mM NaBH$_3$CN as described in Example 1 except that the reaction medium was DMSO/water. The extent of modification and the site of the modification were evaluated by reverse-phase HPLC and Electrospray LCMass Spectrometry (ES LC-MS), as described in Example 1. The results of the HPLC analysis are shown in Table I below.

EXAMPLE 4

Five milligrams of insulin was reacted with 1.25 mg (5.25 mmole) cis-9 hexadecenal and 110 $\mu$l 50 mM NaBH$_3$CN as described in Example 1 except that the reaction medium was Pyridine/water. The extent of modification and the site of the modification were evaluated by reverse-phase HPLC and Electrospray LCMass Spectrometry (ES 1,C-MS), as described in Example 1. The results of the HPLC analysis are shown in Table I below.

EXAMPLE 5

Five milligrams of insulin was reacted with containing 1.25 mg (5.25 mmole) cis-9 hexadecenal and 110 $\mu$l 50 mM NaBH$_3$CN as described in Example 1 except that the reaction medium was 0.5M NaHCO$_3$/isopropanol. The extent of modification and the site of the modification were evaluated by reverse-phase HPLC and Electrospray LCMass Spectrometry (ES LC-MS), as described in Example 1. The results of the HPLC analysis are shown in Table I below.

TABLE I

Percentage of unreacted insulin, mono C16 insulin and di C16 insulin in different reaction media.

| Example* | Peak α (unreacted insulin %) | Peak β (mono C16-insulin %) | Peak γ (di-C16-insulin %) |
|---|---|---|---|
| 1 | 7.2 | 75.9 | 16.9 |
| 2 | 55.2 | 33.6 | 11.2 |
| 3 | 57 | 11 | 32 |
| 4 | 80.2 | 10.2 | 9.6 |
| 5 | 8.8 | 1.5 | 89.7 |

*1) pH 6.8, 1.5M sodiumsalicylate/isopropanal; 2) pH 7.0, 0.1M $NaH_2PO_4$/isopropanol; 3) DMSO/water; 4) Pyridine/water and A) pH 8.5, 0.5M $NaHCO_3$ isopropanol).

As shown in Table I above, the sodium salicylate/isopropranol system generated the largest amount of NB1 1 C16 modified insulin. The 0.5 M $NaHCO_3$/isopropanol system generated large amounts of insulin having two alkyl groups attached thereto. Since this system generates almost no insulin having one alkyl group attached thereto, it is less preferred.

EXAMPLE 6

Five mg of insulin (0.87 mmole) was reacted with 1.25 mg (5.25 mmole) cis-9 hexadecenal and 110 µl 50 mM NaBH3CN in 1 ml of 1.5 M sodium salicylate and 1.2 ml isopropanol as described in example 1 except that the pH of the reaction buffer was 7.8. The peak profile showed no significant difference from the reaction mixture of Example 1, which has a pH value of 6.8 However, the percentage of unreacted insulin was higher.

EXAMPLE 7

Five mg of insulin (0.87 mmole) was reacted with 1.25 mg (5.25 mmole) cis-9 hexadecenal and 110 µl 50 mM NaBH3CN in 1 ml of 1.5 M sodium salicylate and 1.2 ml isopropanol as described in Example 1 except that the pH of the reaction buffer was 10. The extent of modification and the site of the modification were evaluated by reverse-phase HPLC and Electrospray LCMass Spectrometry (ES LC-MS), as described in Example 1. At pH 10, the HPLC analysis gave 52% of unreacted insulin (Peak A), indicating that the reaction rate was slower at higher pH values. The peak cluster (Peak B) was 32% at the 1 C16 insulin region, and the broadness of the peak possibly indicated the existence of 1 C16 insulin isomers. The peak cluster (Peak C) in 2 C16 region was 16%.

EXAMPLE 8

Five milligrams of insulin (0.87 mmole) in 1 ml of 1.5 M sodium salicylate solution was allowed to react with cis-9 hexadecenal except that the amount of cis-9 hexadecenal reacted with the insulin was 0.75 mg. The ratio of aldehyde to $NaBH_3CN$ was kept constant. The volume of isopropanol was 1.2 ml. The extent of modification and the site of the modification were evaluated by reverse-phase HPLC and Electrospray LCMass Spectrometry (ES LC-MS), as described in Example 1. The results are shown in Table II below.

EXAMPLE 9

Five milligrams of insulin (0.87 mmole) in 1 ml of 1.5 M sodium salicylate solution was allowed to react with cis-9 hexadecenal except that the amount of cis-9 hexadecenal reacted with the insulin was 1 mg. The ratio of aldehyde to $NaBH_3CN$ was kept constant. The volume of isopropanol was 1.2 ml. The extent of modification and the site of the modification were evaluated by reverse-phase HPLC and Electrospray LCMass Spectrometry (ES LC-MS), as described in Example 1. The results are shown in Table II below.

EXAMPLE 10

Five milligrams of insulin (0.87 mmole) in 1 ml of 1.5 M sodium salicylate solution was allowed to react with cis-9 hexadecenal except that the amount of cis-9 hexadecenal reacted with the insulin was 2 mg. The ratio of aldehyde to $NaBH_3CN$ was kept constant. The volume of isopropanol was 1.5 ml. The results are shown in Table II below.

EXAMPLE 11

Five milligrams of insulin (0.87 mmole) in 1 ml of 1.5 M sodium salicylate solution was allowed to react with cis-9 hexadecenal except that the amount of cis-9 hexadecenal reacted with the insulin was 3 mg. The ratio of aldehyde to $NaBH_3CN$ was kept constant. The volume of isopropanol was increased to 2.0 ml to solubilize the increased amount of hydrophobic aldehyde. The extent of modification and the site of the modification were evaluated by reverse-phase HPLC and Electrospray LCMass Spectrometry (ES LC-MS), as described in Example 1. The results are shown below in Table II below.

TABLE 2

Percentage of unreacted insulin, mono C16 insulin and di C16 insulin in the sodium salicylate/isopropanol with different insulin-to-aldehyde ratio.

| Insulin:aldehyde (mole/mole) | Peak α (insulin) | Peak β (mono-C16 insulin) | Peak γ (di-C16 insulin) |
|---|---|---|---|
| 1:3.6 | 93.4 | 6.6 | 0 |
| 1:4.8 | 41.3 | 58.7 | 0 |
| 1:6 | 5.7 | 81.7 | 12.5 |
| 1:7.2 | 4.9 | 77.8 | 17.2 |
| 1:9.6 | 3 | 57.4 | 39 |
| 1:14.5 | 4 | 43.7 | 52.2 |

As shown in Table II, the insulin to aldehyde ratio (mol/mol) had an important effect on the yield. For B1 phe site selectivity consideration, insulin to C16 aldehyde ratio was chosen at 1:4.8. Under this condition, almost no 2 C16 modified insulin was present. However, if taken the yield into account, insulin to C16 aldehyde ratio was 1:6. it gave rise the highest yield of B1-hexadecenyl insulin.

EXAMPLE 12
Entrapment of PM into Liposomes
A. Preparation of a lipid matrix.

A solution of chloroform: methanol (2:1) containing 88 mg of sphingomyelin, 24 mg of cholesterol in a 16×100 mm glass tube was evaporated by a stream of nitrogen gas, and the last traces of solvent was removed by attaching the tube to the manifold of a lyophilizer for 15 min. To hydrate the lipid film, 1 ml of 0.9% NaCl solution was added. To form MLVs, the tube was vortexed and sonicated for 30 min at 50° C. (Tc of sphingomyelin is 41° C.). To make dried lipid matrix with highly organized order, the tube was frozen in −80° C. freezer for more than 1 hour and dried by a lyophilizer with temperature set at −50° C.

B. Hydration of lipid matrix with drug solution.

Forty four milligram of PM was dissolved in 1 ml 0.067 M pH 7.4 sodium phosphate buffer solution and a 10 µl aliquot was immediately removed and stored at −80° C. for quantitation of total starting PM. The remaining PM solution was then added to the freeze-dried lipid matrix prepared in section A above. The lipid matrix was hydrated with the solution by vortex mixing and sonication in a cold water bath for 3–5 min to provide a liposome suspension C. Preparation of crude SUV liposomal PM.

Using the "liposofast®" assembly, the liposome suspension was extruded back and forth 11 times through two polycarbonate membranes of 100 nm pore size, followed by another 11 times through two polycarbonate membranes of 50 nm pore size. In this manner the particle size of the liposomes was reduced. To anneal the bilayer packing, the mixture was sonicated for 15 to 30 seconds and kept in ice for 1 hour before separation.

D. Separation of liposome-associated PM and unassociated PM 3 ml mini-columns were packed using Sephadex G50 resin that had been swollen in PBS at 4° C. overnight and degassed. The mini-columns were centrifuged at 450× g (2000 rpm) for 3 min, sealed and kept at 4° C. A 100 $\mu$l aliquot of the crude liposomal PM preparation was loaded onto the top each of the Sephadex G50 minicolumn resting in a 16×10 mm tube followed by adding 400 $\mu$l of PBS. The column assembly was centrifuged 200 g (1,300 rpm) at 4° C. for 1 minute. The eluate was collected immediately as the purified liposomal PM fraction and a 10 $\mu$l aliquot was removed to a tube for PM quantitation and a 10 $\mu$l was removed for lipid quantitation.

E. Characterization i) Yield and PM/lipid ratio,

Each of the above samples was loaded onto the C18 resin columns, which were prewashed with methanol and water, followed by centrifugation at 250 g (1,500 rpm) for 5 minutes at 4° C. Each of the columns was then washed with 0.5 ml ice-cold saline and centrifuge at 1400 g (3500 rpm) for 15 minutes at 4° C. Finally, each column was eluted by 1 ml methanol and was centrifuged at 110 g (1,000 rpm) for 1 min. The eluate was collected onto a 12×75 mm culture tube and the methanol was evaporated under a stream of nitrogen. To each test tube containing the PM residue was added 35 $\mu$l of BSTFA and the tubes were heated at 120° C. in a sand bath for 30 minutes.

The derivertized PM was analyzed by a Finnigan ITS40 ion-trap mass spectrometer couples to a 3300/3400 Varian gas chromatograph. Chemical ionization mode with ammonia as the reagent gas was selected. The ionization current was set at 10 $\mu$l and carrier gas (helium) pressure was set at 15 psi. Oven temperature programmed from 150° C. to 230° C. at a rate of 10° C. per minute. Temperature for injection port was fixed at 220° C., and temperature for transfer line and ion source was set at 280° C. Quantitation was performed using ions at m/z 329 and 333 for derivertized PM and PM-d4, respectively.

The amount of phospholipids in liposomes was analyzed using the method as described in Charles J and Stewart M. Colorimetric determination of phospholipids with ammonium ferrothiocyanate. *Anal. Biochem.* 104:10–14, 1980. Twenty seven grams of ferric chloride hexahydrate (FeCl$_3$.6H2O) and 30.4 g of ammonium thiocyanate (NH$_4$SCN) were dissolved in 1 liter of distilled water. Two milliliters of ferrethiocyanate solution and 2 ml of chloroform were added to 5 $\mu$l of the purified liposomal PM sample (Sample E from Section 4.2) followed by vigorous vortexing for 1 minute and centrifugation at 700 g (2500 rpm) for 5 minutes. The upper layer was removed and discarded and the lower layer was transferred to a 1 cm cuvette for absorbence measurement at 488 nm.

The results indicated that the entrapment efficiency of PM in liposomes prepared by the present method was 10.7% (SD=1.2, n=7). The PM to lipid ratio of the liposomes was from 0.12 to 0.21 $\mu$g/$\mu$g.

ii) Liposome size distribution study. Liposome particle size was measured by a dynamic light scattering BI-90 Particle Sizer. The following parameters were set: duration= 2500 cycles, dust cutoff=21, liquid type=aqueous, refractive index=1.332, temperature 25° C., viscosity=0.89 cp., sample type=vesicle/liposome, RI real=1.590, RI Imag=0.000, parameter K=0.76E-04, and parameter A=−0.53. The sample was properly diluted with distilled water and transferred into a 1 cm dust-free disposable cuvette which was placed into the BI-90 particle sizer.

The size distribution of liposomes prepared by the present method was mono-modal and 80% of the liposomes were within 50–160 nm range for all seven batches of liposomal PM prepared. The mean diameter was 97.2 nm (SD=10.6). At ten days after preparation, the there were no significant changes in the particle size distribution and in the mean diameter and the 10%–90% size range of the liposomes prepared by the present method iii) Stability of liposomes in PBS at 4° C. and 37° C., and in human plasma at 37° C.

At several time intervals, a 10 $\mu$l aliquot of liposomal PM was removed for total PM, liposome associated PM, and leaked PM quantitation. This initial 10 $\mu$l aliquot was diluted in 190 $\mu$l PBS. The separation of entrapped PM and leaked PM was carried out immediately by size exclusion with centrifugation at 4° C. A 25 ul aliquot of the diluted sample was removed and spiked with 2000 ng PM-d8 as internal standard for the leaked PM. Another 25 $\mu$l aliquot of the diluted sample was removed and added to 475 ul of PBS. This sample was loaded onto the pre-prepared 3 ml minicolumn of Sephadex G50. The eluate was collected using centrifugation (200 g,1 minute) as liposome-associated PM and mixed with 1000 ng PM-d4. Each sample or standard was loaded onto the pre-conditioned 3 ml minicolumn of Sephadex G50 by centrifugation of 200 g for 1 minute. The column was then washed twice with 500 $\mu$l PBS and centrifuged at 200 g for 1 minute. Finally, the leaked PM and its internal standard were eluted by 500 $\mu$l PBS and centrifuged at 450 g for 1 minute.

The results indicated that there was about 5% leakage of PM in the initial 15 hours. However the leakage declined to an undetectable rate so that little further leakage of PM was evident at 90 hours. The half life of entrapped PM was about 58 hours at 4° C. in PBS. At 37° C. the liposome associated PM has the half life around 30 minutes both in PBS and in human plasma. These stability results indicate that the present method of preparing liposomes did not induce any packing defects on liposome bilayers.

EXAMPLE 13

Entrapment of Menadiol Sodium Bisulfite into Liposomes

Menadiol sodium Bisulfite was entrapped as in liposomes as described in example 2.

The results indicated that the entrapment efficiency for menadiol sodium bisulfte in the liposomes was about 20% with a drug to lipid ratio of about 0.3 mol/mol.

EXAMPLE 14

Preparation of NB1-cis-9-hexadecenyl insulin incorporated liposomes.

SUV liposomes composed of sphingomyelin and cholesterol (2:1 mol/mol) were prepared as described in example 13 by hydrating the lipid matrix with Tris-EDTA PBS buffer, followed by a brief sonication and extrusion with the "Liposofas®" assembly for 11 cycles through two polycarbonate membranes of 50 nm pore size to provide a liposome suspension.

One milligram of NB1-cis-9-hexadecenyl insulin prepared as described in Example 1 was dissolved in 1 ml Tris-EDTA PBS buffer and mixed with 1 ml of SUV liposome suspension (lipid concentration around 9 mg/ml). The mixture was incubated in a 9–10° C. water bath for 5 minutes with brief sonication (total sonication time was about 1 minute).

To separate the free NB-1-cis-9-hexadecenyl from liposomes, five hundred microliters of the incubated mixture containing liposome and NB1-cis-9-hexadecenyl insulin suspension was loaded dropwise onto a column of Sepharose CL-4B beads equilibrated with Tris-EDTA PBS buffer and packed into a 10×1 cm pipette tip. The column was centrifuged at 28 g (500 rpm) for 30 seconds. The column was eluted with 0.5 ml Tris-EDTA PBS buffer by centrifugation at 28 g (500 rpm) for 30 seconds. The first two eluates were discarded. The elution was then repeated twice and the eluates which contained the pure NB1-cis-9hexadecenyl insulin incorporated liposomes were collected. A control was carried out at the same time with 0.5 ml of 0.5 mg/ml NB1-cis-9-hexadecenyl insulin loaded onto a packed column in the same fashion. Under the same condition, no free NB1-cis-9-hexadecenyl insulin was eluted in the 3rd and 4th elutions.

Characterization of the Liposomes.

A. Lipid to Insulin Ratio

A 100 $\mu$l aliquot of the purified insulin incorporated liposomes was removed for insulin quantitation using BCA assay. The absorbance of the sample was measured at 562 nm. A 10 $\mu$l aliquot of the purified product was removed for lipid quantitation using ferrothiocyanate assay. The results indicated that the average insulin to lipid ratio of these liposomes was 0.027 ($\mu$g/$\mu$g) or 1:300 (mol/mol).

B. Binding to Hepatoma Cells

The ability of the C16 insulin and C-16 insulin incorporated liposomes to bind to hepatoma cells was assayed using HepG2 cells. HepG2 is a human hepatoma cell line that is widely used in as an vitro model for hepatocellular carcinoma. HepG2 possesses a number of insulin receptors (120,000 site/cell) which have been shown to have a high internalization rate (T1/2=2–3 min) upon the binding to insulin.

To perform the assay, semiconfluent cultures of the HepG2 cells were washed twice with cell binding media (MEM with 0.1% bovine serum and 20 mM HEPES, pH 7.8) and then incubated in 1 ml fresh binding medium containing $^{125}$I-Insulin and appropriate amount of insulin or its lipid derivatives at 4° C. for 2 hours. Each dish was washed twice with 5 ml chilled Hank's media to remove unbound insulin. The cells in each dish were detached with 1 ml of 0.01% sodium dodecyl sulfate (SDS) and transferred to a 12×77 mm plastic tube for y-radiation counting. The total binding was determined with 10 pM $^{125}$I-insulin and various modified insulin concentration (0 to 0.1 mM), whereas the nonspecific binding was determined in the presence of 2 mM of insulin with 10 pmol, $^{125}$I-insulin. The results indicated that NB1-cis-9-hexadecenyl insulin had high binding affinity to insulin receptors with Kd=5.72×10 −9 M, which was only three fold lower than that of the unmodified bovine insulin (Kd=1.87×10$^{-9}$ M). NB1-cis-9-hexadecenyl insulin incorporated liposomes showed the similar high binding affinity (Kd=6.37×10$^{-9}$ M) as free NB1-cis-9-hexadecenyl insulin.

EXAMPLE 15

Preparation of Liposomes Containing PM and Having NB1-Lipid Modified Insulin Associated Therewith One milligram of NB1-cis-9-hexadecenyl insulin prepared as described in Example 1A was dissolved in 1 ml Tris-EDTA PBS buffer and mixed with 1 ml of SUV liposome suspension (lipid concentration around 9 mg/ml) prepared as described in Example 3. The liposomes contained PM The mixture was incubated in a 9–10° C. water bath for 5 minutes with brief sonication (total sonication time was around 1 minute).

In order to evaluate the size and the homogeneity of this liposomal formulation, a two-step drop method was adopted for negative stain electron microscopy. A drop of liposome sample was placed on a carbon coated grid. After two minutes, the drop was drawn off by touching the edge of the grid with the torn edge of a piece of filter paper held at 900 to the plane of the grid. Without allowing the film to remain on the grid to dry, liposome drop was replaced by a drop of negative stain (0.2% phosphotungistic acid). After two minutes, the drop of stain was drawn off. The grid was allowed to dry completely. The grid was viewed, within 3 hours after the preparation, with an electron microscope. At least 6 fields which contains approximately 500 liposomes were photographed. Eight by ten inches enlargements were printed from the electron micrograph negatives for the measurement of the diameters of individual liposomes. For ellipsoid or irregular-shaped liposomes the diameter was calculated as the mean of the diameters of the major and minor axis. For disc shaped liposomes, the diameter was equal to 0.71 timed the diameter of the measured disc. In order to determined the size distribution, measured liposome diameters are arbitrarily assigned into predetermined size range. The number of measured liposomes in each range was summed to give a frequency distribution for statistical evaluation.

Cytotoxicity of the liposomes was assayed by the Sulforhodamine B (SRB) assay. In the SRB assay, the property of Sulforhodamine B that stains protein under weakly acidic condition is used as the quantitative indication of cell number.

About 2.5×10$^3$ HepG2 cells/well are incubated with 200 $\mu$l cell culture media, and allowed to attach to plates overnight. Before exposure to any agents, cells are washed twice with binding medium (insulin-free, 0.1% BSA, 20 mM Hepe MEM pH 7.4). Fifty microliter of drug agents at different concentrations are added to wells which contains 200 $\mu$l cell binding media. Following exposure to the cytotoxid agent-containing medium, the cells are washed and then incubated in 200 $\mu$l fresh cell culture media at 37° C. for another 96 hours. Cells are then fixed by gentle layering of 50 $\mu$l of cold (40 C) 50% TCA on the top of the growth medium in each well, followed by incubation at 4° C. for 1 hour. Cell plates are rinsed and allowed to dry. Cells in each well are stained with 50 pd 0.4% SRB in 1% acetic acid for 10 min at the room temperature. Following staining, wells are quickly rinsed five times with 1% acetic acid to remove the unbound dye and allowed to dry. Bound dye in each well is dissolved by addition of 200 $\mu$l of 10 mM unbuffered Tris base (pH 10.5) for 30 min at room temperature prior to plate reading. Plates are read on a microplate reader at wavelength of 490 nm. Control experiments with free PM and liposomal PM are conducted at the same time. To confirm that the increased cytotoxicity of insulin incorporated liposomal PM is mediated by the insulin receptor, cells are pretreated with 2×10$^5$ M insulin for 2 hr in 4° C. before their exposure with insulin incorporated liposomal PM.

To confirm that the increased cytotoxicity is due to the increased drug uptake, cell uptake experiment is conducted. Because no radiolabled PM is available at present, GC-MS method is selected for quantitation.

About 1×10⁷ cells are inoculated with 15 ml growing media in a 75 cm² flask, and allowed to attach the flask overnight. Before exposure to any agent, cells are washed twice with the binding media (insulin free, 0.01% BSA, 20 mM HEPE MEM, pH7.8). To each flask are added the chemical agents in 5 ml binding media and the final PM concentration is around 150 JIM. Triplicates are performed for each agent. After cells are exposed for 1.5 or 3 hours, flasks are transferred to an ice bucket. A 40 pLI aliquot of cell media is removed from each flask for PM quantitation. Duplicates are performed. To remove the surface bound PM, the binding media in each flask is replaced by 10 ml cold dissociation media (insulin free, 0.01% BSA, MEM, pH 4), followed by 3 min incubation on ice and further rinse with ice-cold Hank's media 10 ml twice. Two thousand nanograms of PM-d4 is then added as the internal standard for PM quantitation and 5 ml of 0.01% SDS is added to lyse the cells. A 25 µl aliquot of the mixture is removed from each flask for protein quantitation, and the rest of the mixture is collected for PM quantitation. Controls of free PM and liposomal PM is conducted at the same time. To confirm that this uptake is insulin receptor endocytosis mediated, before the cell uptake experiment, another three flasks of the HepG2 cells are pretreated with high concentration of insulin (2×10⁵M) at 4° C. for 2 hr, which will block the insulin receptors for further binding.

Although specific embodiments of this invention has been shown and described, various adaptations and modifications can be made without departing from the scope of the invention as defined in the appended claims.

What is claimed is:

1. A method of making a lipid-modified insulin molecule comprising:
   (a) reacting insulin and an aliphatic aldehyde in a reaction medium in the presence of a reducing agent to provide a mixture comprising lipid-modified insulin molecules, wherein said aliphatic aldehyde comprises a straight chain alkyl group or olefin group comprising from about 14 to about 20 carbon atoms, and wherein said lipid-modified insulin molecules are linked to said straight chain alkyl or olefin group by an amine linkage; and
   (b) purifying said lipid-modified insulin molecules from said mixture.

2. The method of claim 1 wherein said reducing agent is sodium cyanoborohydride.

3. A method of making a lipid-modified insulin molecule comprising:
   (a) reacting insulin and an aliphatic aldehyde in sodium salicylate and isopropanol in the presence of a reducing agent to provide a mixture comprising lipid-modified insulin molecules, wherein said lipid-modified insulin molecules are linked to said aliphatic aldehye by an amine linkage; and
   (b) purifying said lipid-modified insulin molecules from said mixture.

4. A method of making a lipid-modified insulin molecule comprising:
   (a) reacting insulin and an aliphatic aldehyde in a reaction medium in the presence of a reducing agent to provide a mixture comprising lipid-modified insulin molecules, wherein said lipid-modified insulin molecules are linked to said aliphatic aldehyde by an amine linkage; and
   (b) purifying said lipid-modified insulin molecules from said mixture by a differential C18 solid phase extraction procedure which employs an elution medium comprising from about 0.05% to about 0.1% TFA and methanol or acetonitrile.

5. The method of claim 4 wherein said elution medium comprises a solution of from about 30% to about 100% methanol or acetonitrile.

6. A liposome for delivering a cytotoxic agent to hepatoma cells, said liposome comprising:
   (a) a lipid bilayer defining a compartment; and
   (b) an insulin molecule linked to an alkyl group comprising from about 14 to about 20 carbon atoms or to an olefin group comprising from about 14 to about 20 carbon atoms, said insulin molecule being linked to said alkyl group or said olefin group by an amine linkage, said insulin molecule being associated with said lipid bilayer.

7. The liposome of claim 6 wherein said liposome further comprises a ctyotoxic agent within said compartment.

8. The liposome of claim 6 wherein said alkyl group or said olefin group is linked to the B1 phenylalanine or the B29 lysine of the insulin molecule.

9. The liposome of claim 6 wherein the liposome is a small unilamellar vesicle having a particle size of less than 100 nm.

10. The liposome of claim 7 wherein the ratio of the cytotoxic drug to lipid is greater that 0.12 to 1.0.

11. The liposome of claim 7 wherein the cytotoxic agent is selected from the group consisting of phosphoramide mustard, menadione, doxorubicin, and daunorubicin.

12. The liposome of claim 6 wherein the lipid bilayer comprises sphingomyelin and cholesterol.

13. A method of killing hepatoma cells comprising the steps of:
   (a) providing liposomes comprising a lipid bilayer defining a compartment, a cytotoxic agent within said compartment, and a lipid-modified insulin associated with said lipid bilayer, said lipid modified insulin comprising an insulin molecule linked by an amine linkage to a straight chain alkyl group comprising from about 14 to about 20 carbon atoms or to an olefin group comprising from about 14 to about 20 carbon atoms; and
   (b) contacting said hepatoma cells with said liposomes.

14. The method of claim 13 wherein said cytotoxic agent is selected from the group consisting of phosphoramide mustard, menadione, doxorubicin and daunorubicin.

15. The method of claim 13 wherein said liposome is contacted with said hepatoma cells by injecting said liposome into a patient with hepatocellular carcinoma.

16. The method of claim 1 wherein said reaction mixture comprises sodium salicylate and isopropanol.

17. The method of claim 1 wherein said lipid-modified insulin molecules are purified from the mixture by a differential C18 solid phase extraction procedure which employs an elution medium comprising from about 0.05% to about 0.1% TFA and methanol or acetonitrile.

18. The method of claim 3 wherein said aliphatic aldehyde comprises a straight chain alkyl or olefin group.

19. The method of claim 18 wherein said alkyl group or said olefin group comprises from about 14 to about 20 carbon atoms.

20. The method of claim 4 wherein said aliphatic aldehyde comprises a straight chain alkyl or olefin group.

21. The method of claim 20 wherein said alkyl group or said olefin group comprises from about 14 to about 20 carbon atoms.

* * * * *